United States Patent
Rainis (10) Patent No.: US 9,936,858 B2
(45) Date of Patent: Apr. 10, 2018

(54) COLOR REDUCTION IN IMAGES OF AN INTERIOR OF A HUMAN BODY

(71) Applicant: ORPHEUS MEDICAL LTD., Haifa (IL)

(72) Inventor: David Rainis, Haifa (IL)

(73) Assignee: ORPHEUS MEDICAL LTD, Haifa (IL)

( * ) Notice: Subject to any disclaimer, the term of this patent is extended or adjusted under 35 U.S.C. 154(b) by 178 days.

(21) Appl. No.: 14/765,483

(22) PCT Filed: Feb. 3, 2014

(86) PCT No.: PCT/IL2014/050118
§ 371 (c)(1),
(2) Date: Aug. 3, 2015

(87) PCT Pub. No.: WO2014/118786
PCT Pub. Date: Aug. 7, 2014

(65) Prior Publication Data
US 2015/0359413 A1   Dec. 17, 2015

Related U.S. Application Data (60) Provisional application No. 61/760,241, filed on Feb. 4, 2013.

(51) Int. Cl.
*G06K 9/00* (2006.01)
*A61B 1/00* (2006.01)
(Continued)

(52) U.S. Cl.
CPC ........ *A61B 1/00009* (2013.01); *A61B 1/0002* (2013.01); *A61B 1/04* (2013.01);
(Continued)

(58) Field of Classification Search
CPC ..................................................... H04N 1/644
See application file for complete search history.

(56) References Cited

U.S. PATENT DOCUMENTS 5,625,759 A * 4/1997 Freeman .............. H04N 9/8042
348/384.1
5,673,065 A * 9/1997 DeLeeuw ................ G09G 5/02
345/593

(Continued)

FOREIGN PATENT DOCUMENTS

WO    2014/118786    8/2014

OTHER PUBLICATIONS

Doolittle MH et al., "Color images in telepathology: how many colors do we need?" Hum Pathol. Jan. 1997;28(1):36-41.

(Continued)

*Primary Examiner* — Gandhi Thirugnanam
(74) *Attorney, Agent, or Firm* — Sughrue Mion, PLLC (57) ABSTRACT

Apparatus and methods are described including apparatus (21) for capturing and processing a color video of an interior of a body of a human subject (20). The apparatus (21) includes a medical scope imaging device (22) configured to capture the video, and a medical image processing system (24), which includes a memory (26) and a processor (28). The memory (24) stores a color-reduction table (30), which specifies a plurality of low-occurrence-rate colors. The processor (28) is configured to use the color-reduction table (30) to identify for replacement one or more of the low-occurrence-rate colors in at least one of the frames of the video, and to replace one or more instances of each of the identified low-occurrence-rate colors with a replacement color. Other applications are also described.

20 Claims, 7 Drawing Sheets

(51) Int. Cl.
*H04N 1/64* (2006.01)
*G09G 5/02* (2006.01)
*A61B 1/04* (2006.01)

(52) U.S. Cl.
CPC .............. *G09G 5/02* (2013.01); *H04N 1/644* (2013.01); *A61B 1/00011* (2013.01); *G09G 2340/02* (2013.01); *G09G 2340/0428* (2013.01); *G09G 2360/16* (2013.01); *G09G 2380/08* (2013.01)

(56) References Cited

U.S. PATENT DOCUMENTS

| | | | | |
|---|---|---|---|---|
| 5,877,819 | A * | 3/1999 | Branson | G06F 19/321 348/620 |
| 7,587,097 | B2 * | 9/2009 | Truitt | A61B 3/14 382/254 |
| 7,613,335 | B2 * | 11/2009 | McLennan | G06K 9/4652 382/128 |
| 7,818,042 | B2 * | 10/2010 | Granger | G06T 7/0012 382/128 |
| 2002/0090140 | A1 * | 7/2002 | Thirsk | G06T 9/00 382/239 |
| 2003/0123721 | A1 * | 7/2003 | Megiddo | G06F 17/30256 382/159 |
| 2004/0240716 | A1 * | 12/2004 | de Josselin de Jong | A61B 5/0088 382/128 |
| 2008/0226148 | A1 * | 9/2008 | Gu | G06T 5/007 382/128 |
| 2010/0097452 | A1 * | 4/2010 | Torre-Bueno | H04N 9/045 348/61 |
| 2010/0182414 | A1 * | 7/2010 | Suzuki | H04N 9/74 348/71 |
| 2010/0328740 | A1 * | 12/2010 | Tsukada | H04N 1/6086 358/530 |
| 2015/0359413 | A1 * | 12/2015 | Rainis | H04N 1/644 382/128 |

OTHER PUBLICATIONS

"ImageMagick v6 Examples—Video Handling," http://www.imagemagick.org/Usage/video/, dated Oct. 7, 2010.

U.S. Appl. No. 61/760,241, filed Feb. 4, 2013.

"Solutions. Cases," http://www.mediphan.com/casestudies_Laparoscopic.php, downloaded about Jun. 2011.

Mediphan | Diagnostic Image Capture | Case Studies, http://www.mediphan.com/casestudies_Laparoscopic.php, downloaded about Jun. 2011.

Shah NS, "Lights, lap-camera, tele-action!" http://www.remoteguidance.org/laparascopic-surgery/lights-lap-camera-tele-action/, dated Jun. 19, 2008.

Arnold M et al., "Quality improvement of endoscopy videos," School of Computer Science and Statistics, Trinity College, Dublin 2, Ireland, downloaded about Jun. 2011.

Yang Z et al., "Real-Time 3D Video Compression for Tele-Immersive Environments," Department of Computer Science, University of Illinois at Urbana-Champaign, downloaded about Jun. 2011.

Kumar R, "On color transfer usign sic motion estimation and its application to color video compression," Dhirubhai Ambani Institute of Information & Communication Technology, Gandhinagar, Gujarat, Apr. 2005.

Kim N. et al., "DWT-based scene-adaptive color quantization," Journal Real-Time Imaging—Special issue on multi-dimensional image processing archive, vol. 11 Issue 5-6, Oct.-Dec. 2005 Academic Press Ltd. London, UK.

An International Search Report and a Written Opinion both dated May 13, 2014, which issued during the prosecution of Applicant's PCT/IL2014/050118.

An International Preliminary Report on Patentability dated Aug. 4, 2015, which issued during the prosecution of Applicant's PCT/IL2014/050118.

* cited by examiner

COLOR REDUCTION IN IMAGES OF AN INTERIOR OF A HUMAN BODY

CROSS-REFERENCE TO RELATED APPLICATIONS

The present application is the U.S. national stage of International Application PCT/IL2014/050118, filed Feb. 3, 2014, which claims the benefit of U.S. Provisional Patent Application 61/760,241, filed Feb. 4, 2013, which is assigned to the assignee of the present application and is incorporated herein by reference.

FIELD OF THE INVENTION

The present invention relates in general to apparatus and methods for color reduction.

BACKGROUND

Certain applications, especially in the context of telemedicine, call for effective compression of medical images. In particular, a relatively large compression ratio is desired for color images, which typically comprise a relatively large number of bits. Effective compression of images may facilitate more efficient storage of the images and/or transmission of the images over a computer network.

SUMMARY OF THE INVENTION

The inventors have observed that the interiors of respective human bodies do not vary greatly with respect to the colors that naturally occur therein, and furthermore, that a significant number of colors do not occur at all in the body, or occur with relatively low frequency. The inventors have also observed that instances of a color in an image may be replaced with a similar color, without the human eye being able to notice the difference, as long as the number of instances is not too large. Furthermore, the inventors have observed that reducing the variation of color in an image facilitates compression of the image with a higher compression ratio. Embodiments of the present invention thus provide techniques for reduction of color to increase the compression ratio of compressed color images of an interior of a human body.

The first observation mentioned above is based on the analysis of several color videos of respective interiors of several human bodies. The inventors computed an occurrence rate of each of the possible approximately 32 million colors in each of the videos, and observed relatively little variation between the videos. In other words, the observed distribution of color did not vary greatly between different human bodies. Furthermore, around 25% of the full range of possible colors did not occur at all in the videos, while another relatively large number of colors occurred with relatively low occurrence rates.

The second observation mentioned above is based on the performance of a trial in which several physicians were shown videos in which patches of a first color had been replaced with patches of a second, similar color. The trial was performed for various size patches and for various degrees of similarity between the first and second colors. On average, for patch sizes below a particular threshold, and/or for similarity above a particular threshold, the physicians did not notice the replacement of the patches.

The third observation mentioned above is based on the comparison of compression ratios of compressed "simple" videos with compression ratios of "complex" videos, where the simple videos had less color variation than the complex videos. The compression ratios of the simple videos were higher than those of the complex videos.

As described in further detail hereinbelow, the present invention provides apparatus and methods for color reduction in images of an interior of a body of a human subject. The reduction of color is performed using a color-reduction table, which specifies low-occurrence-rate colors that have a low occurrence rate in images of interiors of human bodies, and may also specify respective replacement colors for the low-occurrence-rate colors. The apparatus includes a medical image processing system, which includes a memory in which the color-reduction table is stored, along with a processor.

A medical scope imaging device captures a video of the interior of the subject's body. The processor receives at least one of the frames of the video, and, using the color-reduction table, replaces one or more pixels in the frame that have a low-occurrence-rate color with a replacement color. The replacement color is similar to the low-occurrence-rate color and has a higher rate of occurrence than the low-occurrence-rate color. Since the replacement color has a higher rate of occurrence than the replaced color, the variation of color in the frame is reduced. Since the replacement color is similar to the replaced color, the difference between the processed frame and the original frame is unnoticeable, or is almost unnoticeable, to the human eye. In general, the reduction of color facilitates a smaller compressed frame size (i.e., a greater compression ratio), such that (a) less storage space is needed to store the compressed frame(s), and/or (b) the compressed frame(s) can be transmitted using less bandwidth.

As described in further detail hereinbelow, the present invention also provides apparatus and methods for generating the color-reduction table. The apparatus includes at least one medical scope imaging device configured to capture a number of sample color images of interiors of one or more human bodies. The apparatus also includes a processor, which calculates respective rates of occurrence for colors occurring in the sample images, and based on the calculated rates of occurrence, generates the color-reduction table.

There is therefore provided, in accordance with some applications of the present invention, apparatus for capturing and processing a color video of an interior of a body of a human subject, the apparatus including:

a medical scope imaging device configured to capture the video of the interior of the body of the human subject, the video including a plurality of frames; and a medical image processing system including:
  a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold; and
  a processor configured to:
    receive at least one of the frames of the video,
    use the color-reduction table to identify for replacement one or more of the low-occurrence-rate colors in the at least one of the frames, and
    replace one or more instances of each of the identified low-occurrence-rate colors with a replacement color that is similar to the identified low-occurrence-rate color and has a rate of occurrence in the sample images that is higher than a rate of occurrence of the identified low-occurrence-rate color.

In some applications, the processor is configured to:

using the color-reduction table, identify that a color of a first pixel of the at least one of the frames is a first one of the low-occurrence-rate colors that is to be replaced, replace the color of the first pixel with a replacement color that is similar to the color of the first pixel, after replacing the color of the first pixel, identify, using the color-reduction table, that a color of a second pixel of the at least one of the frames is a second one of the low-occurrence-rate colors that is to be replaced, and replace the color of the second pixel with a replacement color that is similar to the color of the second pixel, the second one of the low-occurrence-rate colors is a color selected from the group consisting of: the first one of the low-occurrence-rate colors, and a color that is distinct from the first one of the low-occurrence-rate colors.

In some applications, the processor is configured to iteratively process a plurality of pixels of the at least one of the frames by:

(i) for a first one of the plurality of pixels, using the color-reduction table to ascertain whether a color of the pixel is to be replaced, and, if the color of the pixel is to be replaced, (a) identifying a replacement color for the color of the pixel, and (b) replacing the color of the pixel with the replacement color, and (ii) repeating step (i) for each of a remainder of the plurality of pixels.

In some applications, the sample images do not include any images of the interior of the body of the subject.

In some applications, the video is of a given portion of the interior of the body of the human subject, and the sample images do not include any images of portions of the interiors of the human bodies that are distinct from the given portion.

In some applications, each of at least 90% of the sample images includes an image acquired using the medical scope imaging device.

In some applications, each of the sample images includes an image acquired using the medical scope imaging device.

In some applications, the medical scope imaging device is a first medical scope imaging device of a given type, and each of at least 90% of the sample images includes an image acquired using a second medical scope imaging device of the given type, which second medical scope imaging device is distinct from the first medical scope imaging device.

In some applications, the rate of occurrence in the sample images of the replacement color is higher than the occurrence-rate threshold.

In some applications, for each of the identified low-occurrence-rate colors, the replacement color is within a given distance of the identified low-occurrence-rate color.

In some applications, the occurrence-rate threshold is a first occurrence-rate threshold, and the processor is configured to use the color-reduction table to identify for replacement the one or more of the low-occurrence-rate colors at least by ascertaining that respective rates of occurrence in the sample images of the one or more of the low-occurrence-rate colors are lower than a second occurrence-rate threshold, the second occurrence-rate threshold being less than the first occurrence-rate threshold.

In some applications, the processor is further configured to (a) periodically calculate a score that is indicative of a degree to which the identified low-occurrence-rate colors have been replaced in the frame, and (b) lower the second occurrence-rate threshold in response to the score.

In some applications, the occurrence-rate threshold is a first occurrence-rate threshold, and the processor is further configured to:

periodically calculate a score that is indicative of a degree to which the identified low-occurrence-rate colors have been replaced in the frame, in response to the score, identify a second occurrence-rate threshold that is less than the first occurrence-rate threshold, and identify for replacement at least some of the one or more of the low-occurrence-rate colors by ascertaining that respective rates of occurrence in the sample images of the at least some of the one or more of the low-occurrence-rate colors are lower than the second occurrence-rate threshold.

In some applications, the color-reduction table further specifies one or more colors that are not low-occurrence-rate colors.

In some applications, the processor is further configured to, following the replacing of the low-occurrence-rate colors in the frame, compress the frame.

In some applications, the processor is further configured to transmit the compressed frame over a computer network.

In some applications, the color-reduction table further specifies respective replacement colors for the low-occurrence-rate colors.

There is further provided, in accordance with some applications of the present invention, a method of processing a color video, captured by a medical scope imaging device, of an interior of a body of a human subject, the video including a plurality of frames, the method including:

receiving, by a medical image processing system, at least one of the frames of the video, the medical image processing system including (a) a processor, and (b) a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold;

identifying for replacement, by the processor using the color-reduction table, one or more of the low-occurrence-rate colors in the at least one of the frames; and replacing, by the processor, one or more instances of each of the identified low-occurrence-rate colors with a replacement color that is similar to the identified low-occurrence-rate color and has a rate of occurrence in the sample images that is higher than a rate of occurrence of the identified low-occurrence-rate color.

In some applications, the method includes:

identifying, by the processor using the color-reduction table, that a color of a first pixel of the at least one of the frames is a first one of the low-occurrence-rate colors that is to be replaced, replacing, by the processor, the color of the first pixel with a replacement color that is similar to the color of the first pixel, after replacing the color of the first pixel, identifying, by the processor using the color-reduction table, that a color of a second pixel of the at least one of the frames is a second one of the low-occurrence-rate colors that is to be replaced, and replacing, by the processor, the color of the second pixel with a replacement color that is similar to the color of the second pixel, the second one of the low-occurrence-rate colors is a color selected from the group consisting of: the first one of the low-occurrence-rate colors, and a color that is distinct from the first one of the low-occurrence-rate colors.

In some applications, the method includes iteratively processing, by the processor, a plurality of pixels of the at least one of the frames, by:

(i) for a first one of the plurality of pixels, using the color-reduction table to ascertain whether a color of the pixel is to be replaced, and, if the color of the pixel is to be replaced, (a) identifying a replacement color for the color of the pixel, and (b) replacing the color of the pixel with the replacement color, and (ii) repeating step (i) for each of a remainder of the plurality of pixels.

In some applications, the sample images do not include any images of the interior of the body of the subject.

In some applications, the video is of a given portion of the interior of the body of the human subject, and the sample images do not include any images of portions of the interiors of the human bodies that are distinct from the given portion.

In some applications, each of at least 90% of the sample images includes an image acquired using the medical scope imaging device.

In some applications, each of the sample images includes an image acquired using the medical scope imaging device.

In some applications, the medical scope imaging device is a first medical scope imaging device of a given type, and each of at least 90% of the sample images includes an image acquired using a second medical scope imaging device of the given type, which second medical scope imaging device is distinct from the first medical scope imaging device.

In some applications, the rate of occurrence in the sample images of the replacement color is higher than the occurrence-rate threshold.

In some applications, replacing the one or more instances of each of the identified low-occurrence-rate colors with the replacement color that is similar to the identified low-occurrence-rate color includes replacing the one or more instances of each of the identified low-occurrence-rate colors with a replacement color that is within a given distance of the identified low-occurrence-rate color.

In some applications, the occurrence-rate threshold is a first occurrence-rate threshold, and using the color-reduction table to identify for replacement the one or more of the low-occurrence-rate colors in the at least one of the frames includes ascertaining that respective rates of occurrence in the sample images of the one or more of the low-occurrence-rate colors are lower than a second occurrence-rate threshold, the second occurrence-rate threshold being less than the first occurrence-rate threshold.

In some applications, the method further includes:

periodically calculating, by the processor, a score that is indicative of a degree to which the identified low-occurrence-rate colors have been replaced in the frame; and lowering the second occurrence-rate threshold in response to the score.

In some applications, the occurrence-rate threshold is a first occurrence-rate threshold, and the method further includes:

periodically calculating, by the processor, a score that is indicative of a degree to which the identified low-occurrence-rate colors have been replaced in the frame;

in response to the score, identifying, by the processor, a second occurrence-rate threshold that is less than the first occurrence-rate threshold; and identifying for replacement at least some of the one or more of the low-occurrence-rate colors by ascertaining that respective rates of occurrence in the sample images of the at least some of the one or more of the low-occurrence-rate colors are lower than the second occurrence-rate threshold.

In some applications, the color-reduction table further specifies one or more colors that are not low-occurrence-rate colors.

In some applications, the method further includes, following the replacing of the low-occurrence-rate colors in the frame, compressing the frame by the processor.

In some applications, the method further includes transmitting the compressed frame over a computer network.

In some applications, the color-reduction table further specifies respective replacement colors for the low-occurrence-rate colors.

There is further provided, in accordance with some applications of the present invention, apparatus including:

at least one medical scope imaging device configured to capture a plurality of sample color images of interiors of one or more human bodies; and a processor configured to:

calculate respective rates of occurrence for a plurality of colors occurring in the sample images, and based on the calculated rates of occurrence, generate a color-reduction table that specifies a plurality of low-occurrence-rate colors, the respective rates of occurrence in the sample images of the low-occurrence-rate colors being lower than an occurrence-rate threshold.

In some applications, the processor is further configured to populate the color-reduction table with one or more colors that are not low-occurrence-rate colors.

In some applications, the at least one medical scope imaging device includes exactly one medical scope imaging device.

In some applications, the processor is further configured to:

identify respective replacement colors for the low-occurrence-rate colors, the replacement colors being similar to the low-occurrence-rate colors, respectively; and populate the color-reduction table with the respective replacement colors for the low-occurrence-rate colors.

In some applications, the processor is configured to identify the respective replacement colors for the low-occurrence-rate colors by identifying that the replacement colors are less than a given distance from the respective low-occurrence-rate colors.

There is further provided, in accordance with some applications of the present invention, a method including:

capturing, with at least one medical scope imaging device, a plurality of sample color images of interiors of one or more human bodies;

calculating, by a processor, respective rates of occurrence for a plurality of colors occurring in the sample images;

based on the calculated rates of occurrence, generating, by the processor, a color-reduction table that specifies a plurality of low-occurrence-rate colors, the respective rates of occurrence in the sample images of the low-occurrence-rate colors being lower than an occurrence-rate threshold; and storing, by the processor, the generated color-reduction table in a computer memory.

In some applications, generating the color-reduction table includes populating the table with one or more colors that are not low-occurrence-rate colors.

In some applications, using the at least one medical scope imaging device includes using exactly one medical scope imaging device.

In some applications, generating the color-reduction table includes:

identifying, by the processor, respective replacement colors for the low-occurrence-rate colors, the replacement colors being similar to the low-occurrence-rate colors, respectively; and populating the color-reduction table with the respective replacement colors for the low-occurrence-rate colors.

In some applications, identifying the respective replacement colors for the low-occurrence-rate colors includes identifying that the replacement colors are less than a given distance from the respective low-occurrence-rate colors.

There is further provided, in accordance with some applications of the present invention, a method of processing a color video of an interior of a body of a human subject, the method including:

capturing, by a medical scope imaging device, the video of the interior of the body of the human subject, the video including a plurality of frames, receiving, by a medical image processing system, at least one of the frames of the video, the medical image processing system including (a) a processor, and (b) a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold;

identifying for replacement, by the processor using the color-reduction table, one or more of the low-occurrence-rate colors in the at least one of the frames; and replacing, by the processor, one or more instances of each of the identified low-occurrence-rate colors with a replacement color that is similar to the identified low-occurrence-rate color and has a rate of occurrence in the sample images that is higher than a rate of occurrence of the identified low-occurrence-rate color.

In some applications, the method includes:

identifying, by the processor using the color-reduction table, that a color of a first pixel of the at least one of the frames is a first one of the low-occurrence-rate colors that is to be replaced, replacing, by the processor, the color of the first pixel with a replacement color that is similar to the color of the first pixel, after replacing the color of the first pixel, identifying, by the processor using the color-reduction table, that a color of a second pixel of the at least one of the frames is a second one of the low-occurrence-rate colors that is to be replaced, and replacing, by the processor, the color of the second pixel with a replacement color that is similar to the color of the second pixel, the second one of the low-occurrence-rate colors is a color selected from the group consisting of: the first one of the low-occurrence-rate colors, and a color that is distinct from the first one of the low-occurrence-rate colors.

In some applications, the sample images do not include any images of the interior of the body of the subject.

In some applications, the video is of a given portion of the interior of the body of the human subject, and the sample images do not include any images of portions of the interiors of the human bodies that are distinct from the given portion.

In some applications, each of at least 90% of the sample images includes an image acquired using the medical scope imaging device.

In some applications, each of the sample images includes an image acquired using the medical scope imaging device.

In some applications, the medical scope imaging device is a first medical scope imaging device of a given type, and each of at least 90% of the sample images includes an image acquired using a second medical scope imaging device of the given type, which second medical scope imaging device is distinct from the first medical scope imaging device.

In some applications, the rate of occurrence in the sample images of the replacement color is higher than the occurrence-rate threshold.

In some applications, replacing the one or more instances of each of the identified low-occurrence-rate colors with the replacement color that is similar to the identified low-occurrence-rate color includes replacing the one or more instances of each of the identified low-occurrence-rate colors with a replacement color that is within a given distance of the identified low-occurrence-rate color.

In some applications, the occurrence-rate threshold is a first occurrence-rate threshold, and using the color-reduction table to identify for replacement the one or more of the low-occurrence-rate colors in the at least one of the frames includes ascertaining that respective rates of occurrence in the sample images of the one or more of the low-occurrence-rate colors are lower than a second occurrence-rate threshold, the second occurrence-rate threshold being less than the first occurrence-rate threshold.

In some applications, the method further includes:

periodically calculating, by the processor, a score that is indicative of a degree to which the identified low-occurrence-rate colors have been replaced in the frame; and lowering the second occurrence-rate threshold in response to the score.

In some applications, the occurrence-rate threshold is a first occurrence-rate threshold, and the method further includes:

periodically calculating, by the processor, a score that is indicative of a degree to which the identified low-occurrence-rate colors have been replaced in the frame;

in response to the score, identifying, by the processor, a second occurrence-rate threshold that is less than the first occurrence-rate threshold; and identifying for replacement at least some of the one or more of the low-occurrence-rate colors by ascertaining that respective rates of occurrence in the sample images of the at least some of the one or more of the low-occurrence-rate colors are lower than the second occurrence-rate threshold.

In some applications, the color-reduction table further specifies one or more colors that are not low-occurrence-rate colors.

In some applications, the method further includes, following the replacing of the low-occurrence-rate colors in the frame, compressing the frame by the processor.

In some applications, the method further includes transmitting the compressed frame over a computer network.

In some applications, the color-reduction table further specifies respective replacement colors for the low-occurrence-rate colors.

The present invention will be more fully understood from the following detailed description of embodiments thereof, taken together with the drawings, in which:

DETAILED DESCRIPTION OF APPLICATIONS

Figure 1:
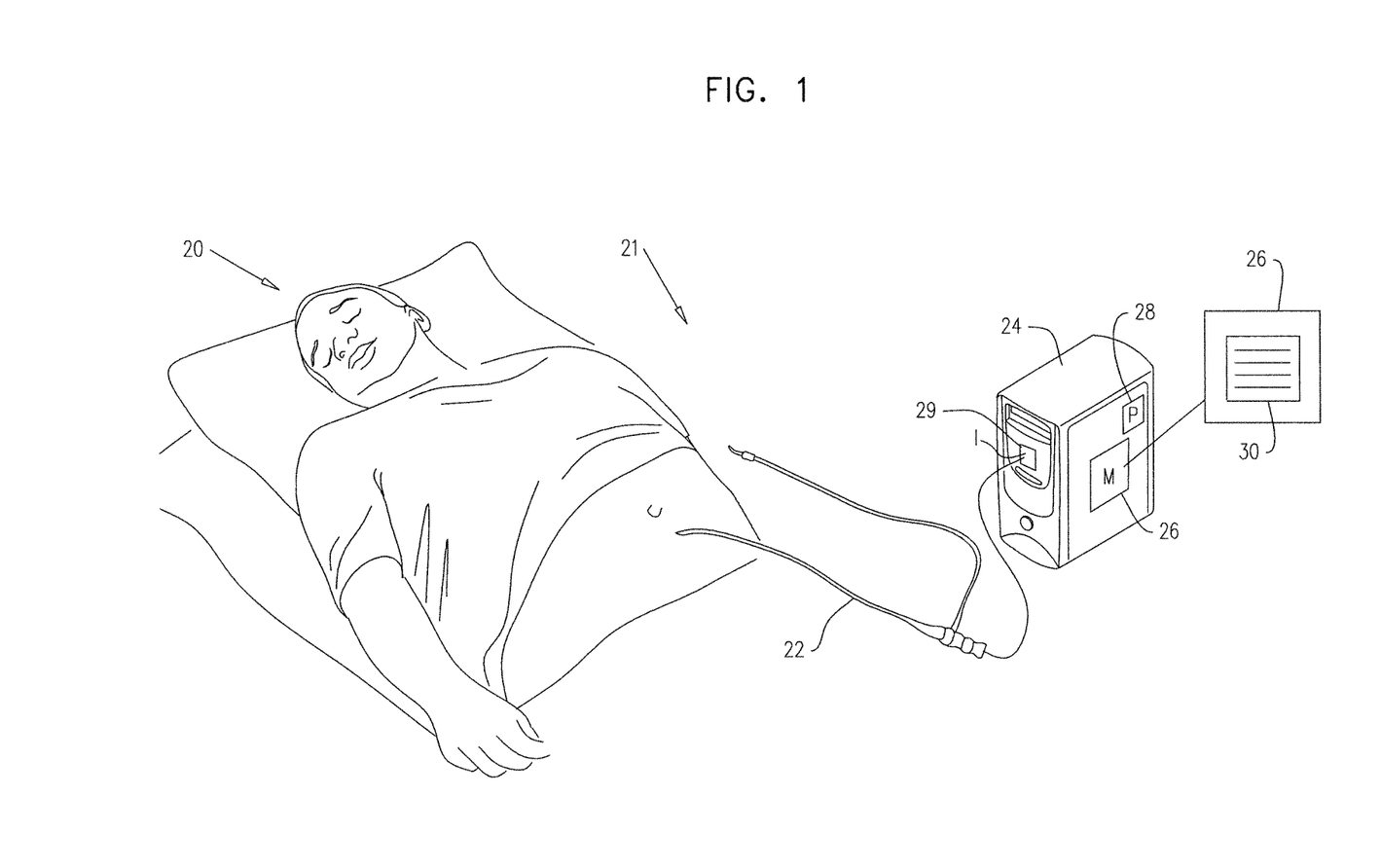
FIG. 1 is a schematic illustration of apparatus for capturing and processing a color video of an interior of a body of a human subject, in accordance with some applications of the present invention.

Reference is made to FIG. 1, which is a schematic illustration of apparatus 21 for capturing and processing a color video of an interior of a body of a human subject 20, in accordance with some applications of the present invention. The apparatus comprises a medical scope imaging device 22, e.g., an endoscope or laparoscope. Medical scope imaging device 22 is configured to capture the video, which includes a plurality of frames. The video may be of any portion of the interior of the body of subject 20, including, for example, the gastrointestinal tract or urinary tract of the subject.

Apparatus 21 further comprises a medical image processing system 24, which comprises a memory 26, a processor 28, along with communication interfaces 29 and software for carrying out the functions prescribed by the present invention. (In some applications, memory 26 and processor 28 may be contained in a single computer, e.g., a work station.) This software may be downloaded to the systems in electronic form over a network, for example, or it may alternatively be supplied on non-transient tangible media, such as CD-ROM. Memory 26 comprises a non-volatile memory, such as one or more hard disk drives, and/or a volatile memory, such as random-access memory (RAM).

Memory 26 stores a color-reduction table 30, which specifies a plurality of low-occurrence-rate colors. As further described hereinbelow with reference to FIG. 2, the low-occurrence-rate colors have respective rates of occurrence in sample color images that are lower than an occurrence-rate threshold. (As used in the present application, including the claims, a "rate of occurrence" or "occurrence rate" is a number of occurrences in a given sample, and may be represented as an absolute value or a normalized value, e.g., a percentage.) For example, if the occurrence-rate threshold is 0.2%, a color that occurs in fewer than 0.2% of the pixels of the sample images is a low-occurrence-rate color. For some applications, the occurrence-rate threshold is at least 0.06%, no greater than 0.8%, and/or between 0.06% and 0.8%. In some applications, the occurrence-rate threshold may be identified as the occurrence rate corresponding to a particular percentile in a histogram of the all of the colors that occur in the sample images. For example, the occurrence rate of the color that falls in the 12th percentile may be identified as the occurrence-rate threshold. For some applications, the percentile is at least the sixth percentile, no greater than the twelfth percentile, and/or between the sixth and the twelfth percentile. In some applications, color-reduction table 30 further specifies one or more colors that are not low-occurrence-rate colors.

Processor 28 is configured to receive the video from imaging device 22, and to use color-reduction table 30 to identify for replacement one or more of the low-occurrence-rate colors in at least one of the frames of the video. (In the context of the claims and specification of the present application, identifying a color for replacement includes (a) identifying that the color occurs at least once in the frame, and (b) identifying that at least one instance of the color is to be replaced.) The processor then replaces one or more instances of each of the identified low-occurrence-rate colors with a replacement color that is similar to the identified low-occurrence-rate color and has a higher rate of occurrence in the sample images than the identified low-occurrence-rate color. (In the context of the claims and specification of the present application, two colors are "similar" to each other if the difference between them is indistinguishable, or nearly indistinguishable, to the human eye. For example, as described immediately below, two colors are similar to each other if the distance between them is relatively small.) In some applications, the replacement color is within a given distance of the identified low-occurrence-rate color, where the distance between the colors may be determined in any color space and using any of the measures for color distance that are known in the art. (For example, in the RGB color space, the distance may be determined as SQRT $(dR^2+dG^2+dB^2)$, where dR, dG, and dB are the respective differences in the R, G, and B channels of the colors.) In some applications, the replacement color is the color within a given distance of the identified low-occurrence-rate color that has the highest occurrence rate in the sample images. In other applications, the replacement color is the closest color whose rate of occurrence is above a particular threshold (e.g., the occurrence-rate threshold that is used to designate the low-occurrence-rate colors). In yet other applications, a formula incorporating both distance (i.e., similarity) and rate of occurrence is used to identify the replacement color.

In some applications, processor 28 identifies for replacement each one of the low-occurrence-rate colors that occurs in the frame. Alternatively, the processor may identify for replacement only those low-occurrence-rate colors that have a rate of occurrence in the sample images that is below a second occurrence-rate threshold, the second occurrence-rate threshold being lower than the first occurrence-rate threshold described above. For example, if, as described above, the first occurrence-rate threshold is 0.2%, the processor may identify for replacement only those colors with an occurrence rate less than 0.1%. The usage of the second occurrence-rate threshold typically allows for flexibility in the degree to which colors are reduced in the frame(s). That is, color-reduction table 30 typically specifies a relatively large number of low-occurrence-rate colors, by utilizing a relatively high first occurrence-rate threshold. For applications in which relatively aggressive color reduction is desired, the second occurrence-rate threshold can be close to or equal to the first occurrence-rate threshold, while for applications in which less aggressive color-reduction is desired, the second occurrence-rate threshold can be lower. In this manner, apparatus 21 is able to accommodate various degrees of color reduction. (As further described hereinbelow with reference to FIG. 6, this flexibility may be further enhanced by adaptive lowering of the second occurrence-rate threshold.)

As described above with respect to the first occurrence-rate threshold, the second occurrence-rate threshold may correspond to a given percentile in the histogram derived from the sample images. For example, if, as described above, the first occurrence-rate threshold corresponds to the 12th percentile, the second occurrence-rate threshold may correspond to the 8th percentile.

The first and second occurrence-rate thresholds might be considered to respectively define "medium" and "low" rates of occurrence. If the first occurrence-rate threshold is used for identifying colors for replacement, both the "low" and "medium" occurrence-rate colors may be reduced, while if the second occurrence-rate threshold is used, the processor may reduce only those colors that have a "low" rate of occurrence. (The usage of the terms "low" and "medium" is by way of illustration only, and other terms may be used. For example, the first threshold can be thought of as corresponding to a "medium-high" rate of occurrence, with the second threshold corresponding to a "medium" rate of occurrence. Additionally, to avoid any possible misunderstanding, it is noted that colors with "medium" rates of occurrence are also low-occurrence-rate colors.) Typically, the respective rates of occurrence in the sample images of the replacement colors are higher than the occurrence-rate threshold. That is, if the low-occurrence-rate colors specified in color-reduction table 30 have "low" and "medium" rates of occurrence, the replacement colors can be considered to have "high" rates of occurrence.

Figure 2:
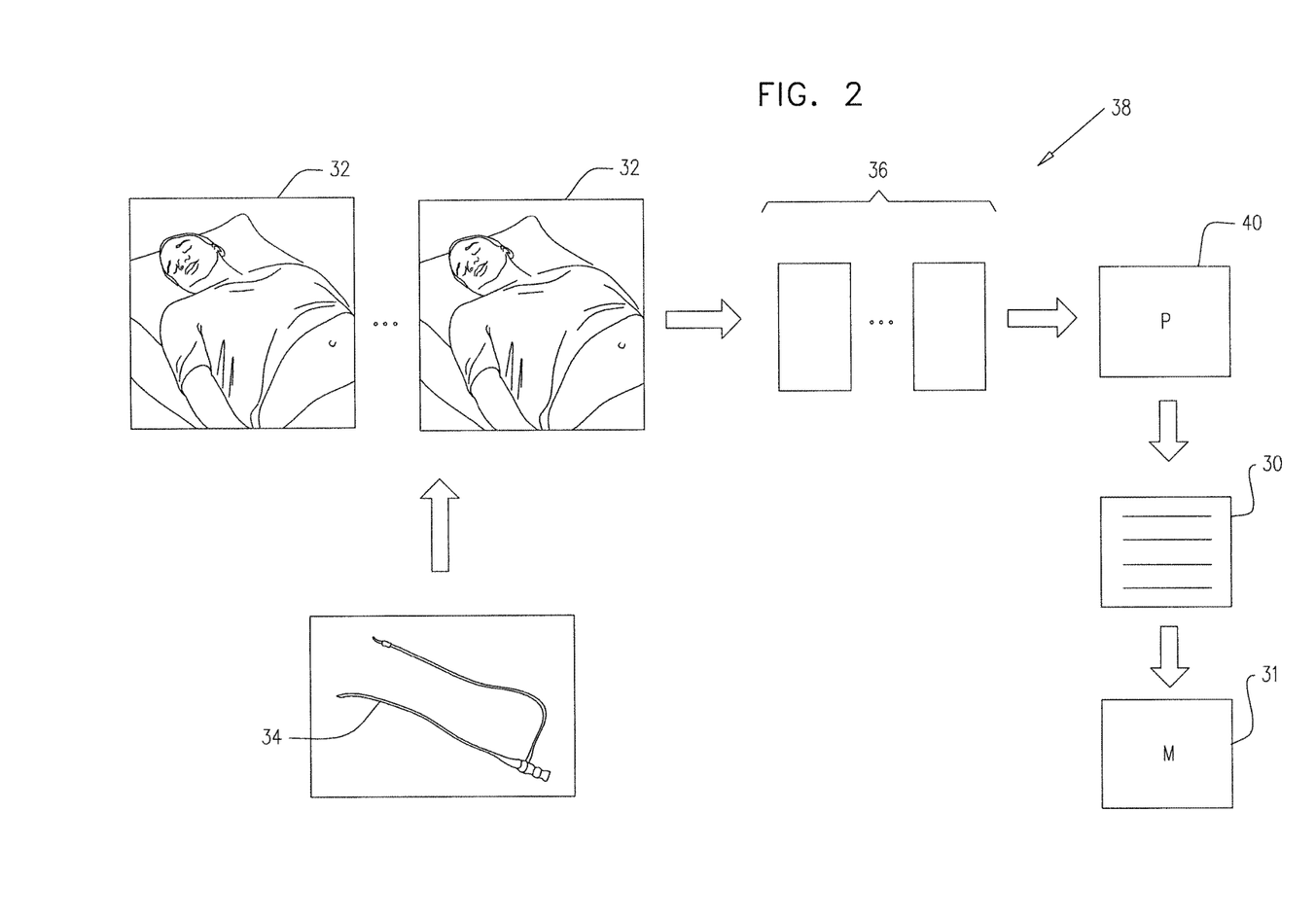
FIG. 2 is a schematic illustration of apparatus for generating a color-reduction table, in accordance with some applications of the present invention.
Figure 3:
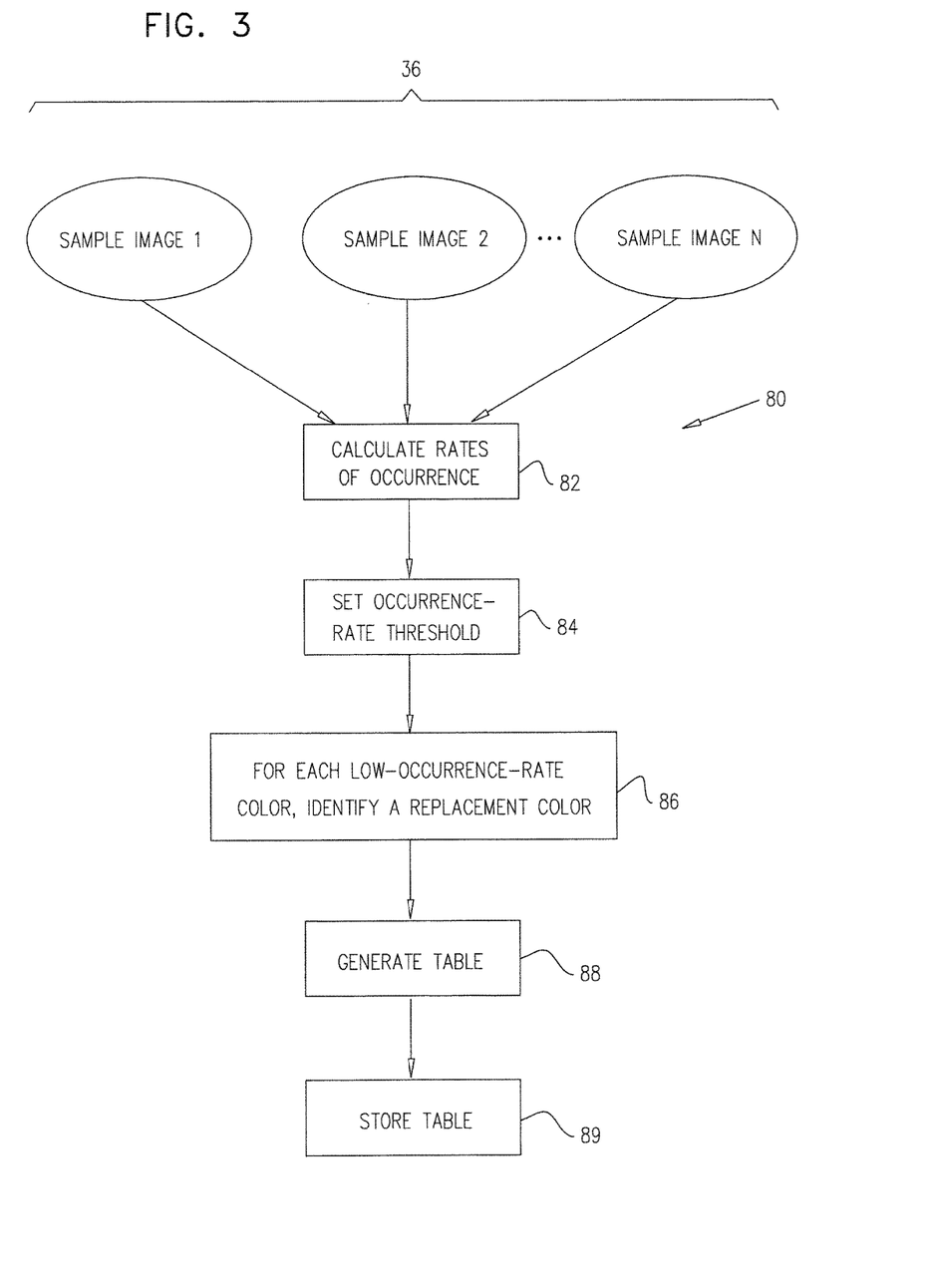
FIG. 3 is a flow chart illustrating a method for generating a color-reduction table, in accordance with some applications of the present invention.

Reference is now made to FIG. 2, which is a schematic illustration of apparatus 38 for generating color-reduction table 30, in accordance with some applications of the present invention. Reference is also made to FIG. 3, which is a flow chart that illustrates a method 80 for generating color-reduction table 30, in accordance with some applications of the present invention. Typically, apparatus 38 is configured to perform method 80 illustrated in the flow chart of FIG. 3.

Apparatus 38 comprises at least one medical scope imaging device 34 configured to capture a plurality 36 of sample color images (e.g., frames of a video) of interiors of one or more human bodies 32. Apparatus 38 further comprises a processor 40, along with communication interfaces and software for carrying out the functions prescribed by the present invention. This software may be downloaded to the systems in electronic form over a network, for example, or it may alternatively be supplied on non-transient tangible media, such as CD-ROM.

Processor 40 is configured to calculate, at a calculation step 82 of method 80, respective rates of occurrence for a plurality of colors occurring in sample images 36. Based on the calculated rates of occurrence, processor 40 is configured to generate, at a table-generation step 88, color-reduction table 30. Typically, processor 40 is further configured to store, at a table-storing step 89, the generated color-reduction table in a memory 31, which comprises a non-volatile memory, such as one or more hard disk drives, and/or a volatile memory, such as random-access memory (RAM). As described hereinabove with reference to FIG. 1, color-reduction table 30 specifies the low-occurrence-rate colors some or all of which are to be reduced in the video that is captured by imaging device 22. The color-reduction table is transferred to memory 26 (FIG. 1), e.g., on a tangible computer-readable medium or over a computer network.

In some applications, processor 40 is further configured to populate color-reduction table 30 with one or more colors that are not low-occurrence-rate colors. For example, the color-reduction table may include every one of the colors (e.g., the approximately 32 million colors) that can possibly occur in a color image, with an occurrence rate specified for each color. Typically, processor 40 is further configured to identify the respective replacement colors for the low-occurrence-rate colors. This identification typically first involves the setting of the occurrence-rate threshold (at a threshold-setting step 84), such that colors with rates of occurrence below the occurrence threshold are low-occurrence-rate colors for which a replacement color must be identified. For each of the low-occurrence-rate colors, a replacement color is identified (at a replacement-color identification step 86), e.g., as described hereinabove with reference to FIG. 1. (For example, the replacement color may be identified as the color within a given distance of the identified low-occurrence-rate color that has the highest occurrence rate in the sample images.) The processor populates color-reduction table 30 with the replacement colors, such that, for example, each low-occurrence-rate color is paired with its replacement color, as further described immediately below.

Color-reduction table 30 is typically generated and stored in memory in a manner such that the low-occurrence-rate colors are associated with their respective occurrence rates, and/or their respective replacement colors. For example, by way of illustration, a small segment of one possible "human-readable" representation of the color-reduction table is shown below:

TABLE 1

| Color (RGB) | Occurrence Rate | Replacement Color (RGB) |
| --- | --- | --- |
| (50, 100, 76) | 0.01% | (52, 98, 79) |
| (87, 140, 200) | 0.098% | (85, 141, 203) |
| (120, 120, 215) | 0.098% | (122, 118, 215) |

The occurrence rate may be specified in the color-reduction table in relative terms, rather than absolute terms. For example, instead of the absolute occurrence rates of each color, the color-reduction table may contain relative terms such as "low", "medium", and "high", or a numerical representation thereof, e.g., 0, 1, and 2. For example, in the sample segment shown above, the row may have "medium" in the second column, with the next two rows having "low" in the second column.

In some applications, there is a certain degree of variability between different image sensors (e.g., CCD image sensors), even among imaging devices of the same type. In such applications, it may be desired to perform the color reduction using a color-reduction table that is specific to the imaging device used to capture the video; hence, imaging device 22 (FIG. 1), which captures the video, also acquires all or a majority, e.g., at least 90%, of the sample images. In some applications, a single medical scope imaging device (e.g., imaging device 22) is used to acquire sample images 36, while in other applications, more than one medical scope imaging device is used. In some applications, color-reduction table 30 is specific to a given type of medical scope imaging device, but not necessarily to a given device. In such applications, a device that is distinct from imaging device 22, but is of the same type as imaging device 22, acquires all or a majority, e.g., at least 90%, of the sample images.

As noted hereinabove in the Summary of the Invention, the inventors have observed that the interiors of respective human bodies do not vary greatly with respect to the colors that naturally occur therein. Accordingly, color-reduction table 30 may be generated without using any data from the body of the particular subject 20 (FIG. 1) who is being imaged. That is, in some applications, sample images 36 do not include any images of the interior of the body of the subject, but are instead captured beforehand from other human bodies.

In some applications, color-reduction table 30 is specific to the given portion of anatomy that is being imaged by imaging device 22. For example, if imaging device 22 is capturing a video of the gastrointestinal tract, the color-reduction table used may be specific to the gastrointestinal tract. It follows that, in such a case, the sample images used to generate color-reduction table 30 do not include any images of a portion of anatomy other than the gastrointestinal tract. In some applications of the present invention, a plurality of color-reduction tables are provided, corresponding, respectively, to different portions of anatomy. Given the plurality of color-reduction tables, an operator may specify the particular color-reduction table that is to be used for a given video.

Figure 4:
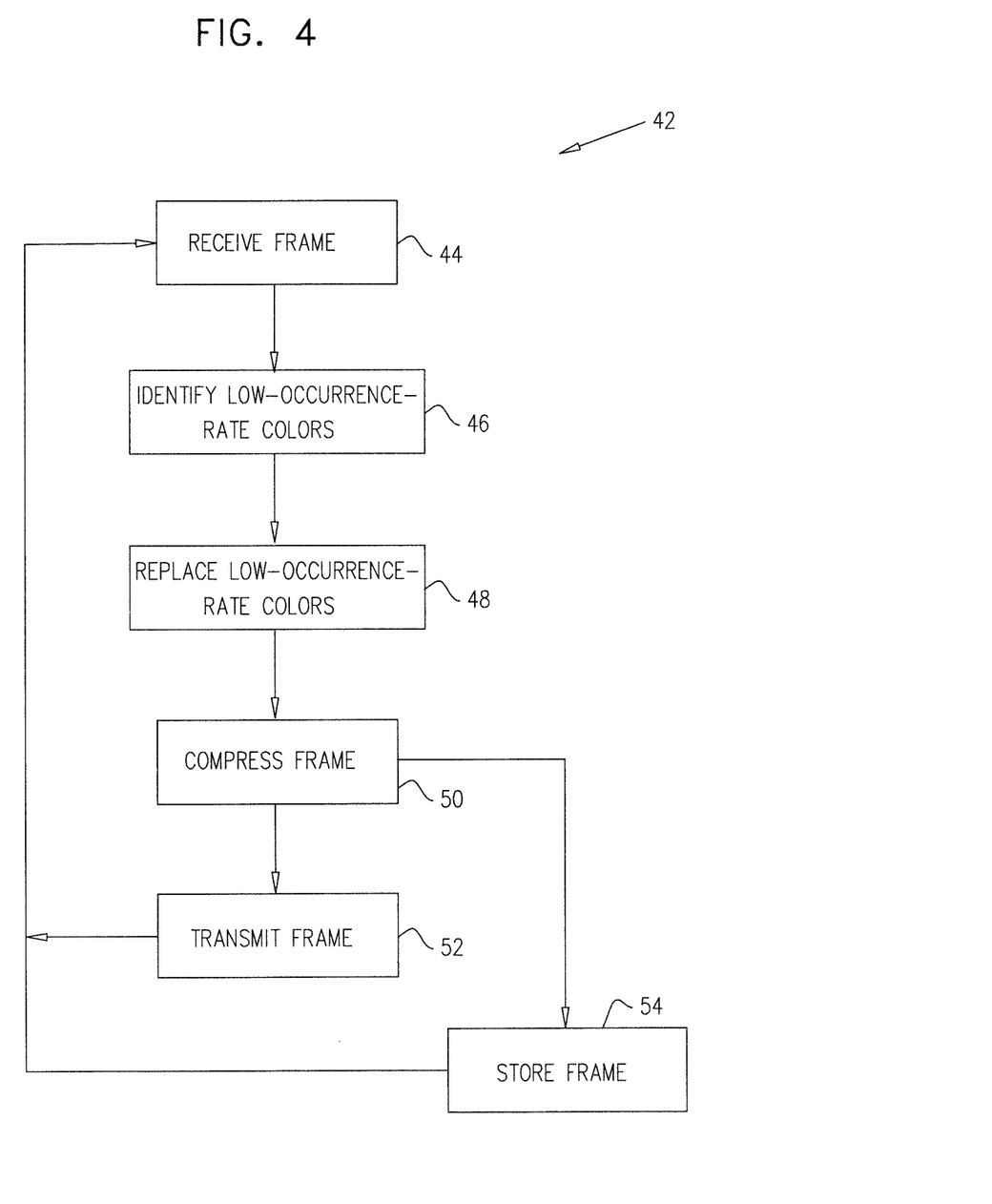
FIG. 4 is a flow chart illustrating a method of processing a color video of an interior of a body of a human subject, in accordance with some applications of the present invention.

Reference is now made to FIG. 4, which is a flow chart illustrating a method 42 of processing a color video of an interior of a body of a human subject, in accordance with some applications of the present invention. At a frame reception step 44, a frame is received from medical scope imaging device 22 by medical image processing system 24 (FIG. 1), typically in real-time. The frame is typically stored in volatile memory, e.g., in a buffer, while the remainder of method 42 is performed.

At a low-occurrence-rate color identification step 46, processor 28 uses color-reduction table 30 to identify for replacement one or more of the low-occurrence-rate colors in the frame, as described above with reference to FIG. 1. At a replacement step 48, processor 28 replaces one or more instances of each of the identified low-occurrence-rate colors with a replacement color, as described above with reference to FIG. 1 and as described in more detail below. Typically, the processor then compresses the frame at a compression step 50. Some applications of the present invention compress a video using standard compression algorithms and protocols, such as compression with the h.264 HE Main codec, in combination with the novel techniques described herein. To avoid any possible misunderstanding, it is noted that the color-reduction techniques described herein are not compression techniques per se. That is, the reduction of color does not in itself necessarily result in smaller image or video sizes. Rather, the color-reduction techniques described herein facilitate more effective compression of images and/or video (i.e., higher compression ratios), by reducing the variation of color in the images and/or video, as described generally in the Summary and as described below with reference to FIGS. 7A-B.

In some applications, the compressed frame is transmitted over a computer network (e.g., a wide-area network, such as the Internet, a wide-area private network, or a private digital line) at a transmission step 52. For simplicity, FIG. 4 shows compression step 50 and transmission step 52 occurring in series with the previous steps. That is, FIG. 4 shows the compression and transmission of a frame occurring before the processing of the next frame begins. However, since some compression algorithms operate on a plurality of consecutive frames, rather than on a single frame, the compression and/or transmission of frames may be performed in parallel to the other steps of the method. For example, following replacement step 48, the frame may be stored in a buffer, and the next frame may be immediately received and processed. Following the accumulation of a number of processed frames in the buffer (the number depending on the compression algorithm), and while steps 44, 46, and/or 48 are being performed, the accumulated frames may be compressed and/or transmitted.

In some applications, as described immediately above, transmission step 52 and/or compression step 50 is performed in real-time. In other applications, one or both of steps 50 and 52 occur "off line," e.g., only after all of the frames in the video have been processed via steps 44, 46, and 48. Alternatively or additionally to transmission step 52, the compressed frame is stored, e.g., on a hard drive or other computer-readable medium, at a storage step 54. As described hereinabove in the Summary of the Invention, the reduction of color that is performed in step 48 facilitates a smaller compressed frame size, such that (a) less storage space is needed to store the compressed frame(s), and/or (b) the compressed frame(s) can be transmitted using less bandwidth. Typically, the method is repeated for a plurality, e.g., all, of the frames that are captured by imaging device 22.

Figure 5:
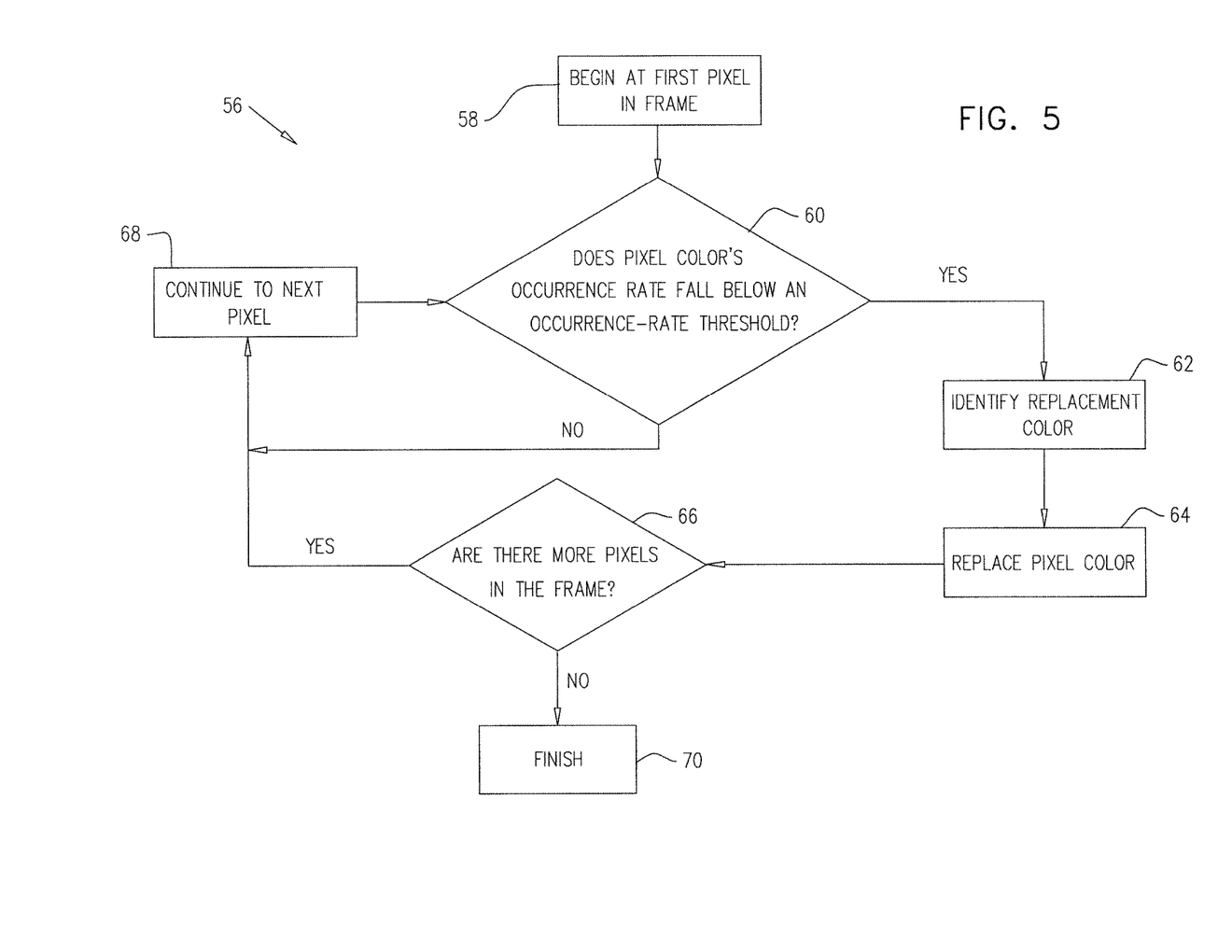
FIG. 5 is a flow chart illustrating a color-reduction algorithm operating on a frame of a captured video, in accordance with some applications of the present invention.

Reference is now made to FIG. 5, which is a flow chart illustrating a color-reduction algorithm 56 operating on a frame of the captured video, in accordance with some applications of the present invention. The algorithm begins at a beginning step 58 by initiating the processing of the first pixel in the frame. (This pixel is "first" in the sense of being the first pixel to be processed, even if it is not at a corner or edge of the frame.) At a comparison step 60, the processor ascertains whether the color of the pixel is to be replaced, by using color-reduction table 30 to determine whether the occurrence rate of the color is below an occurrence-rate threshold. As described hereinabove with reference to FIG. 1, in some applications, the first occurrence-rate threshold is used, such that all low-occurrence-rate colors are identified for replacement, while in other applications, a second, lower occurrence-rate threshold is used.

If the color is identified for replacement, the algorithm identifies the replacement color at a replacement-color identification step 62, typically by looking up the replacement color in color-reduction table 30, and the color of the pixel is replaced with the replacement color at a replacement step 64. At a checking step 66, the algorithm checks whether further pixels remain in the frame. If further pixels remain in the frame, the algorithm continues by processing the next pixel at a continuation step 68, while if not, the processing of the frame ends at a finishing step 70. Algorithm 56 may then operate on the next received frame of the video, as shown in the flow chart of FIG. 4.

Color-reduction algorithm 56 is a particular example of how identification step 46 and replacement step 48 of method 42 (FIG. 4) may be performed by processor 28. In particular, algorithm 56 performs identification step 46 and replacement step 48 in a continual, alternating fashion, such that, for each of the pixels in a plurality of pixels (where the plurality includes, for example, all of the pixels in the frame), the processor (via algorithm 56) iterates over steps 46 and 48. (If the color of a particular pixel is not identified for replacement, replacement step 48 will not be performed that particular pixel.) In this manner, processor 28 uses a one-pass approach, processing each of the plurality of pixels exactly once. For example, the algorithm begins (at beginning step 58) with the first pixel to be processed, i.e., a first one of the plurality of pixels. At comparison step 60, algorithm 56 uses color-reduction table 30 to ascertain whether the color of the pixel is to be replaced. If the algorithm ascertains that the color is to be replaced (i.e., if the algorithm identifies that the color of the pixel is a first one of the low-occurrence-rate colors that is to be replaced), the algorithm proceeds to replacement-color identification step 62. At replacement-color identification step 62, the algorithm identifies a replacement color for the color of the pixel. At replacement step 64, the algorithm then replaces the color of the pixel with the identified replacement color. After replacing the color of the first pixel, the algorithm continues to a second one of the plurality of pixels, at continuation step 68. The second pixel is then processed in a manner that is similar or identical to the manner in which the first pixel was processed. In other words, the algorithm uses color-reduction table 30 to ascertain whether the color of the second pixel is to be replaced. If the algorithm ascertains that the color is to be replaced (i.e., if the algorithm identifies that the color of the pixel is a second one of the low-occurrence-rate colors that is to be replaced), the replacement color for the color of the second pixel is identified, and the replacement is performed. (The second one of the low-occurrence-rate colors may or may not be distinct from the first one of the low-occurrence-rate colors.) The third pixel is then similarly or identically processed, until the entire plurality of pixels has been processed in this manner.

In contrast to the one-pass approach of algorithm 56, in other applications. e.g., the two-pass approach described hereinbelow with reference to FIG. 6, processor 28 performs identification step 46 for the entire plurality of pixels (e.g., for the entire frame), and then performs replacement step 48 for each of the pixels in the plurality of pixels whose color has been identified for replacement. In other words, for each of identification step 46 and replacement step 48, the processor iterates over each of the pixels for which the step is being performed.

Figure 6:
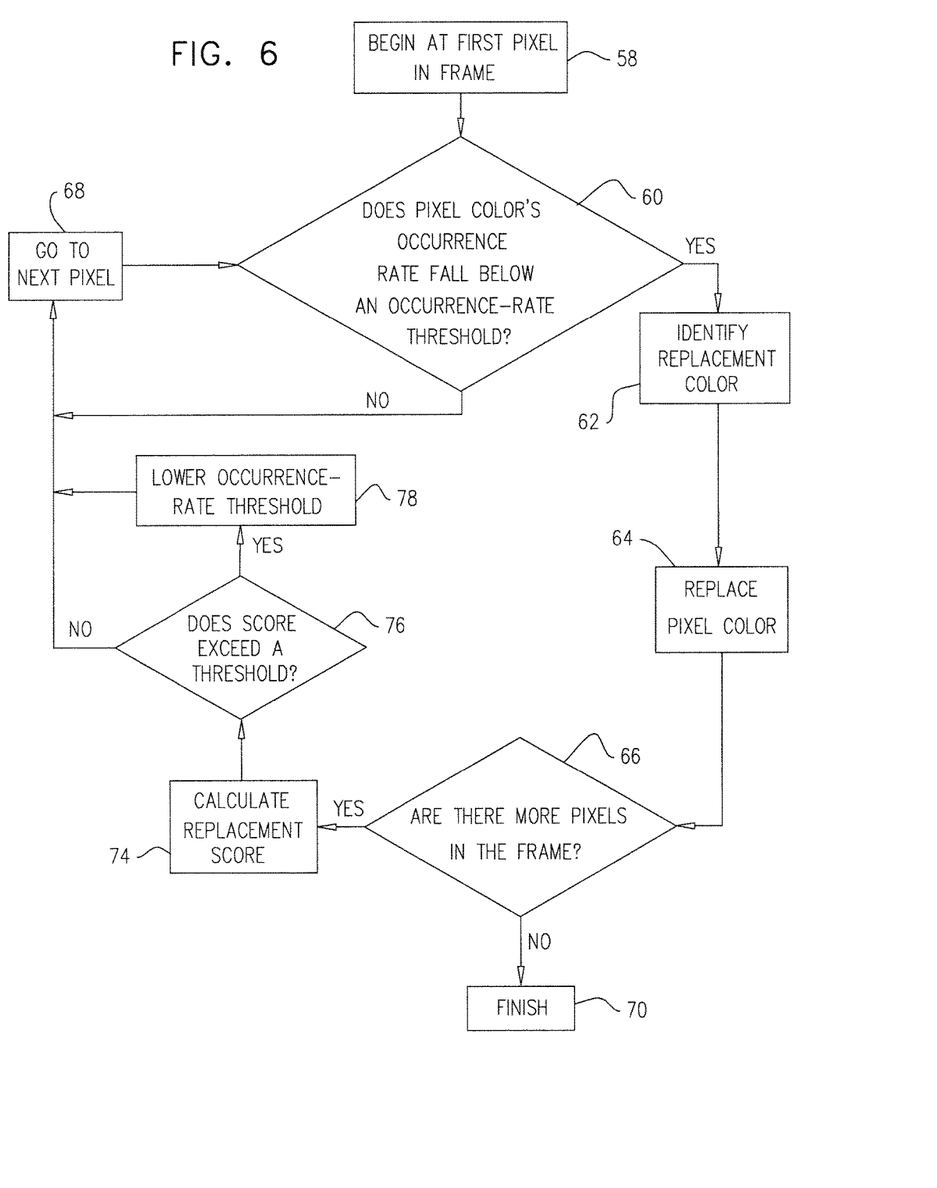
FIG. 6 is a flow chart illustrating another color-reduction algorithm operating on a frame of a captured video, in accordance with some applications of the present invention.

Reference is now made to FIG. 6, which is a flow chart illustrating another color-reduction algorithm 72 operating on a frame of the captured video, in accordance with some applications of the present invention. Color-reduction algorithm 72 includes all of the steps of color-reduction algorithm 56, described hereinabove with reference to FIG. 5, and also includes several additional steps between steps 66 and 68, as will now be described. Like algorithm 56, algorithm 72 is a particular example of how identification step 46 and replacement step 48 of method 42 (FIG. 4) may be performed by processor 28.

As described hereinabove with reference to FIG. 5, algorithm 72 checks (at checking step 66) whether there are more pixels in the frame to be processed. If the algorithm determines that there are more pixels to be processed, the algorithm, at a calculation step 74, calculates a score that is indicative of a degree to which the identified low-occurrence-rate colors have been replaced in the frame. For example, the score may include a number or percentage of pixels whose colors have thus far been replaced, and/or a cumulative distance between the replaced colors and the replacement colors. (To facilitate a smooth reading of the present description, "a pixel whose color has been replaced" may be referred to simply as "a replaced pixel.") At a score comparison step 76, the algorithm then compares the score to a threshold. If the score exceeds the threshold, the algorithm, at a threshold-lowering step 78, lowers the occurrence-rate threshold that is used in comparison step 60 to identify a color for replacement.

For example, the algorithm may begin the processing of the frame by using the first occurrence-rate threshold at comparison step 60, such that all of the low-occurrence-rate colors specified in color-reduction table 30 are identified for replacement. Using the terminology introduced above, this means that the algorithm may begin by identifying for replacement all of the "low" and "medium" occurrence-rate colors. Upon the score exceeding the threshold, e.g., upon the number of replaced pixels exceeding a threshold number of replaced pixels, the algorithm, at threshold-lowering step 78, may switch to a second, lower occurrence-rate threshold, such that, for example, only the "low" occurrence-rate colors are subsequently replaced, while the "medium" occurrence-rate colors are not replaced. Alternatively or additionally, the algorithm may lower the second occurrence-rate threshold at threshold-lowering step 78, in response to the score. Typically, the score is calculated periodically, such as after every N pixel replacements, e.g., after every pixel replacement. The occurrence-rate threshold may be lowered any number of times, in response to the calculated score. In general, the calculating of the score, and the lowering of the occurrence-rate threshold in response thereto, facilitates preventing the color-reduced frame from being noticeably different from the original, by preventing an excessively large number of pixels from being replaced.

In the techniques of color-reduction algorithm 72, the processing of the frame does not restart upon the lowering occurrence-rate threshold at step 78. In such applications, sometimes a first part of the frame is processed using a first occurrence-rate threshold, while another part of the frame is processed using a different occurrence-rate threshold. Other applications, on the other hand, use a two-pass approach. In such applications, the algorithm does a first pass through the frame, during which the algorithm identifies all of the potentially-replaceable pixels in the frame. (During this first pass, no pixels are replaced.) Depending on a desired level of color reduction (e.g., depending on the replacement score threshold), the occurrence-rate threshold to be used at step 60 is identified, and the entire frame is then processed using the identified occurrence-rate threshold.

Figure 7A:
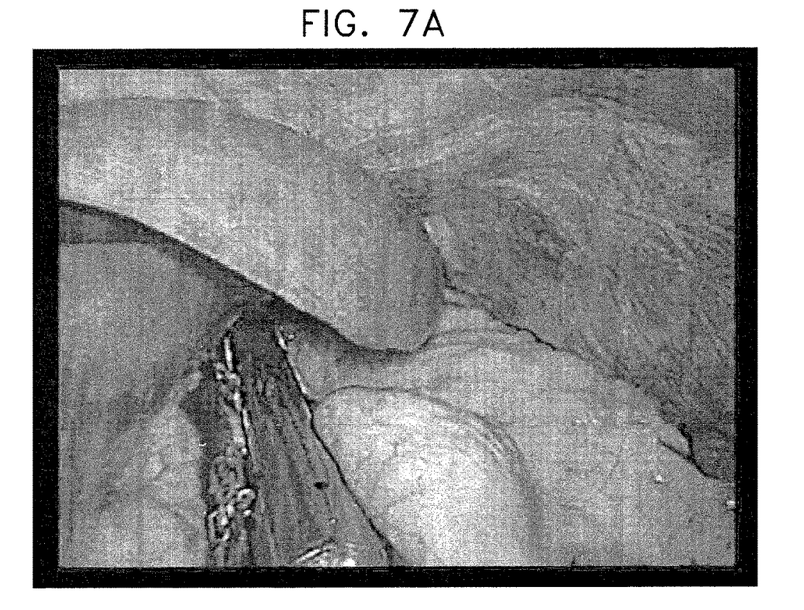
FIGS. 7A-B are original and color-reduced images, respectively, resulting from an application of techniques of the present invention.
Figure 7B:
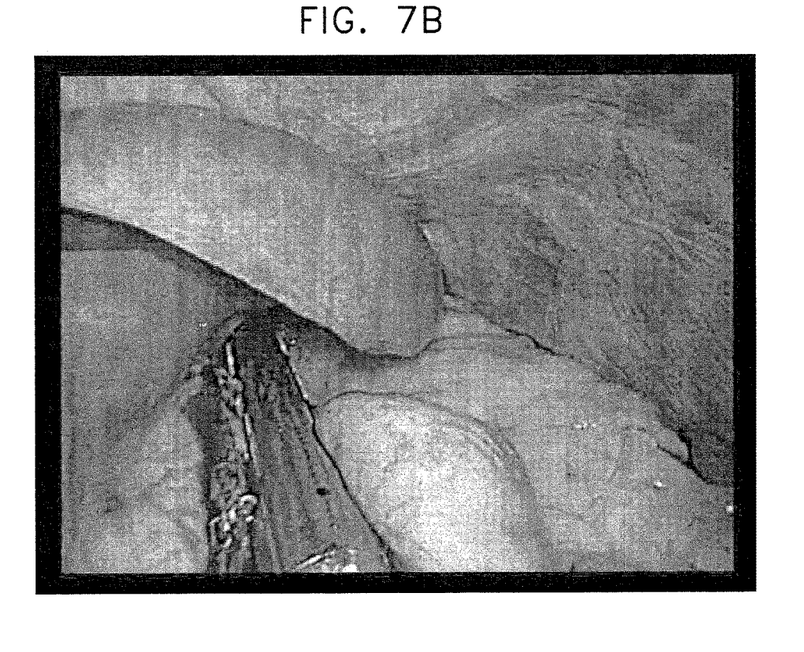

Reference is now made to FIGS. 7A-B, which are original and color-reduced images, respectively, resulting from an application of techniques of the present invention. The inventors performed a trial in which three videos were captured by a laparoscopic camera at the OLD hospital in Aalast, Belgium. Each video comprised frames of size 1280×720 pixels. A 15-minute segment was extracted from each video, and was compressed both with and without prior color reduction. As shown in the table below, the application of color-reduction techniques of the present invention resulted in a significant reduction in the size of the compressed segment:

TABLE 2

| Segment extracted from | Compressed size of segment without prior color reduction | Compressed size of segment with prior color reduction | Reduction in size of compressed segment |
|---|---|---|---|
| Video 1 | 812 MB | 771 MB | 5% |
| Video 2 | 983 MB | 914 MB | 7% |
| Video 3 | 979 MB | 925 MB | 5.5% |

The color-reduced segments were screened, side-by-side with the respective original segments, to four physicians.

(FIG. 7A shows a frame from one of the original segments, while FIG. 7B shows the corresponding frame from the corresponding color-reduced segment.) During each of the screenings, none of the physicians was able to distinguish between the original segment and the color-reduced segment.

Embodiments of the image processing described herein can take the form of an entirely hardware embodiment, an entirely software embodiment or an embodiment including both hardware and software elements. In an embodiment, the invention is implemented in software, which includes but is not limited to firmware, resident software, micro code, etc.

Furthermore, the embodiments of the image processing can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus. Or device. The medium can be an electronic, magnetic, optical, electromagnetic, infrared, or semiconductor system (or apparatus or device) or a propagation medium.

Examples of a tangible computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DAD.

Typically, the operations described herein that relate to storing information to memory transform the physical state of the memory, which is a real physical article, to have a different magnetic polarity, electrical charge, or the like depending on the technology of the memory that is used.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Input/output (I/O) devices (including but not limited to keyboards, displays, pointing devices, etc.) Can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Small talk, C++ or the like and conventional procedural programming languages, such as the C programming language or similar programming languages.

It will be understood that each block of the flowcharts shown in FIGS. 3-6, and combinations of blocks in the flowchart, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart blocks.

It will be appreciated by persons skilled in the art that the present invention is not limited to what has been particularly shown and described hereinabove. Rather, the scope of the present invention includes both combinations and sub combinations of the various features described hereinabove, as well as variations and modifications thereof that are not in the prior art, which would occur to persons skilled in the art upon reading the foregoing description.

The invention claimed is:

1. Apparatus for capturing and processing a color video of an interior of a body of a human subject, the apparatus comprising:
   a medical scope imaging device configured to capture the video of the interior of the body of the human subject, the video including a plurality of frames; and
   a medical image processing system comprising:
      a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold; and
      a processor configured to:
         receive at least one of the frames of the video,
         use the color-reduction table to identify for replacement one or more of the low-occurrence-rate colors in the at least one of the frames, and
         replace one or more instances of each of the identified low-occurrence-rate colors with a replacement color that is similar to the identified low-occurrence-rate color and has a rate of occurrence in the sample images that is higher than a rate of occurrence of the identified low-occurrence-rate color,
   wherein the occurrence-rate threshold is a first occurrence-rate threshold, and
   wherein the processor is further configured to:
      periodically calculate a score that is indicative of a degree to which the identified low-occurrence-rate colors have been replaced in the frame, in response to the score, identify a second occurrence-rate threshold that is less than the first occurrence-rate threshold, and identify for replacement at least some of the one or more of the low-occurrence-rate colors by ascertaining that respective rates of occurrence in the sample images of the at least some of the one or more of the low-occurrence-rate colors are lower than the second occurrence-rate threshold.

2. The apparatus according to claim 1, wherein the processor is configured to:

using the color-reduction table, identify that a color of a first pixel of the at least one of the frames is a first one of the low-occurrence-rate colors that is to be replaced, replace the color of the first pixel with a replacement color that is similar to the color of the first pixel, after replacing the color of the first pixel, identify, using the color-reduction table, that a color of a second pixel of the at least one of the frames is a second one of the low-occurrence-rate colors that is to be replaced, and replace the color of the second pixel with a replacement color that is similar to the color of the second pixel, wherein the second one of the low-occurrence-rate colors is a color selected from the group consisting of: the first one of the low-occurrence-rate colors, and a color that is distinct from the first one of the low-occurrence-rate colors.

3. The apparatus according to claim 1, wherein the processor is configured to iteratively process a plurality of pixels of the at least one of the frames by:

(i) for a first one of the plurality of pixels, using the color-reduction table to ascertain whether a color of the pixel is to be replaced, and, if the color of the pixel is to be replaced, (a) identifying a replacement color for the color of the pixel, and (b) replacing the color of the pixel with the replacement color, and (ii) repeating step (i) for each of a remainder of the plurality of pixels.

4. The apparatus according to claim 1, wherein the sample images do not include any images of the interior of the body of the subject.

5. The apparatus according to claim 1, wherein each of at least 90% of the sample images includes an image acquired using the medical scope imaging device.

6. The apparatus according to claim 1, wherein the medical scope imaging device is a first medical scope imaging device of a given type, and wherein each of at least 90% of the sample images includes an image acquired using a second medical scope imaging device of the given type, which second medical scope imaging device is distinct from the first medical scope imaging device.

7. Apparatus for capturing and processing a color video of an interior of a body of a human subject, the apparatus comprising:

a medical scope imaging device configured to capture the video of the interior of the body of the human subject, the video including a plurality of frames; and a medical image processing system comprising:

a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold; and a processor configured to:
receive at least one of the frames of the video,
use the color-reduction table to identify for replacement one or more of the low-occurrence-rate colors in the at least one of the frames, and
replace one or more instances of each of the identified low-occurrence-rate colors with a replacement color that is similar to the identified low-occurrence-rate color and has a rate of occurrence in the sample images that is higher than a rate of occurrence of the identified low-occurrence-rate color, wherein the occurrence-rate threshold is a first occurrence-rate threshold, and wherein the processor is configured to use the color-reduction table to identify for replacement the one or more of the low-occurrence-rate colors at least by ascertaining that respective rates of occurrence in the sample images of the one or more of the low-occurrence-rate colors are lower than a second occurrence-rate threshold, the second occurrence-rate threshold being less than the first occurrence-rate threshold.

8. The apparatus according to claim 1, wherein the color-reduction table further specifies one or more colors that are not low-occurrence-rate colors.

9. The apparatus according to claim 1, wherein the processor is further configured to, following the replacing of the low-occurrence-rate colors in the frame, compress the frame.

10. The apparatus according to claim 1, wherein the color-reduction table further specifies respective replacement colors for the low-occurrence-rate colors.

11. A method of processing a color video, captured by a medical scope imaging device, of an interior of a body of a human subject, the video including a plurality of frames, the method comprising:

receiving, by a medical image processing system, at least one of the frames of the video, the medical image processing system including (a) a processor, and (b) a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold;

identifying for replacement, by the processor using the color-reduction table, one or more of the low-occurrence-rate colors in the at least one of the frames; and replacing, by the processor, one or more instances of each of the identified low-occurrence-rate colors with a replacement color that is similar to the identified low-occurrence-rate color and has a rate of occurrence in the sample images that is higher than a rate of occurrence of the identified low-occurrence-rate color, wherein the occurrence-rate threshold is a first occurrence-rate threshold, and wherein the method further comprises:
periodically calculating, by the processor, a score that is indicative of a degree to which the identified low-occurrence-rate colors have been replaced in the frame;

in response to the score, identifying, by the processor, a second occurrence-rate threshold that is less than the first occurrence-rate threshold; and identifying for replacement at least some of the one or more of the low-occurrence-rate colors by ascertaining that respective rates of occurrence in the sample images of the at least some of the one or more of the low-occurrence-rate colors are lower than the second occurrence-rate threshold.

12. The method according to claim 11, wherein the method comprises:
identifying, by the processor using the color-reduction table, that a color of a first pixel of the at least one of the frames is a first one of the low-occurrence-rate colors that is to be replaced,
replacing, by the processor, the color of the first pixel with a replacement color that is similar to the color of the first pixel,
after replacing the color of the first pixel, identifying, by the processor using the color-reduction table, that a color of a second pixel of the at least one of the frames is a second one of the low-occurrence-rate colors that is to be replaced, and
replacing, by the processor, the color of the second pixel with a replacement color that is similar to the color of the second pixel,
wherein the second one of the low-occurrence-rate colors is a color selected from the group consisting of: the first one of the low-occurrence-rate colors, and a color that is distinct from the first one of the low-occurrence-rate colors.

13. The method according to claim 11, wherein the method comprises iteratively processing, by the processor, a plurality of pixels of the at least one of the frames, by:
(i) for a first one of the plurality of pixels, using the color-reduction table to ascertain whether a color of the pixel is to be replaced, and, if the color of the pixel is to be replaced, (a) identifying a replacement color for the color of the pixel, and (b) replacing the color of the pixel with the replacement color, and
(ii) repeating step (i) for each of a remainder of the plurality of pixels.

14. The method according to claim 11, wherein the sample images do not include any images of the interior of the body of the subject.

15. The method according to claim 11, wherein each of at least 90% of the sample images includes an image acquired using the medical scope imaging device.

16. The method according to claim 11, wherein the medical scope imaging device is a first medical scope imaging device of a given type, and wherein each of at least 90% of the sample images includes an image acquired using a second medical scope imaging device of the given type, which second medical scope imaging device is distinct from the first medical scope imaging device.

17. A method of processing a color video, captured by a medical scope imaging device, of an interior of a body of a human subject, the video including a plurality of frames, the method comprising:
receiving, by a medical image processing system, at least one of the frames of the video, the medical image processing system including (a) a processor, and (b) a memory in which a color-reduction table is stored, the color-reduction table specifying a plurality of low-occurrence-rate colors having respective rates of occurrence in sample color images of interiors of one or more human bodies, which rates of occurrence are lower than an occurrence-rate threshold;
identifying for replacement, by the processor using the color-reduction table, one or more of the low-occurrence-rate colors in the at least one of the frames; and
replacing, by the processor, one or more instances of each of the identified low-occurrence-rate colors with a replacement color that is similar to the identified low-occurrence-rate color and has a rate of occurrence in the sample images that is higher than a rate of occurrence of the identified low-occurrence-rate color,
wherein the occurrence-rate threshold is a first occurrence-rate threshold, and
wherein using the color-reduction table to identify for replacement the one or more of the low-occurrence-rate colors in the at least one of the frames comprises ascertaining that respective rates of occurrence in the sample images of the one or more of the low-occurrence-rate colors are lower than a second occurrence-rate threshold, the second occurrence-rate threshold being less than the first occurrence-rate threshold.

18. The method according to claim 11, wherein the color-reduction table further specifies one or more colors that are not low-occurrence-rate colors.

19. The method according to claim 11, further comprising, following the replacing of the low-occurrence-rate colors in the frame, compressing the frame by the processor.

20. The method according to claim 11, wherein the color-reduction table further specifies respective replacement colors for the low-occurrence-rate colors.

* * * * *